United States Patent [19]
Brodsky

[11] 4,157,093
[45] Jun. 5, 1979

[54] HYGIENE SYSTEM
[76] Inventor: Ralph H. Brodsky, 14 E. 81 St., New York, N.Y. 10028
[21] Appl. No.: 876,381
[22] Filed: Feb. 9, 1978
[51] Int. Cl.² .............................................. A61M 3/00
[52] U.S. Cl. ..................................... 128/225; 128/251
[58] Field of Search ............... 128/225, 224, 229, 230, 128/251, 66, 239

[56] References Cited
U.S. PATENT DOCUMENTS

| | | | |
|---|---|---|---|
| 528,232 | 10/1894 | Lundholm | 128/225 |
| 1,522,601 | 1/1925 | Strobel | 128/225 |

*Primary Examiner*—John D. Yasko
*Attorney, Agent, or Firm*—Ladas, Parry, Von Gehr, Goldsmith & Deschamps

[57] ABSTRACT

A system for oral and vaginal hygiene and for contraceptive use comprising a source of compressed air having a compressed air outlet, an output connector means attached to control flow from the outlet, a first spray device for oral hygiene adapted for connection to the connector means to received compressed air from the source and a second spray and irrigation device for vaginal hygiene and contraceptive use adapted for connection to the connector means to receive compressed air from the source, wherein the first spray device, which has a first liquid container and a first elongate output probe having a spray nozzle at one end, is actuated by compressed air received by way of the connector means to eject a spray of liquid from the container through the nozzle and wherein the second spray and irrigation device, which has a second liquid container, a second elongate output probe having a spray nozzle at one end and a control valve movable between first and second operative positions, is actuated by compressed gas received by way of the connector means to eject a spray from a nozzle of the second output probe, the spray produced by the second spray device in the first position of the valve consisting solely of a stream of liquid from the container and in the second position of the valve consisting of a mixture of liquid from the container and compressed air from the source.

7 Claims, 7 Drawing Figures

U.S. Patent   Jun. 5, 1979   4,157,093
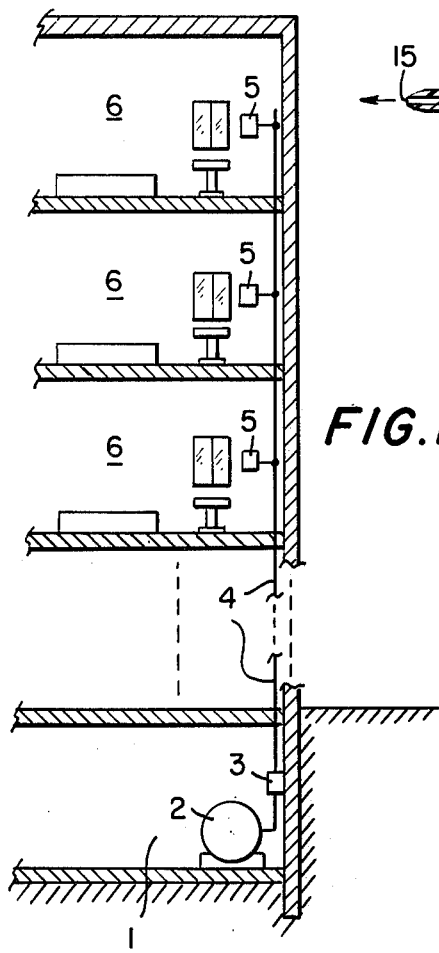
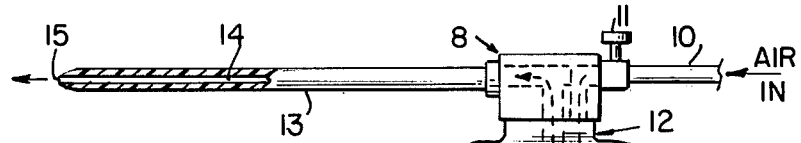
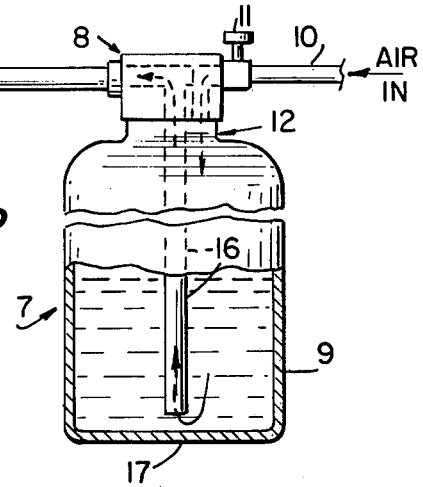
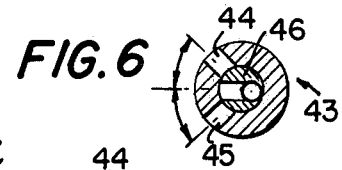
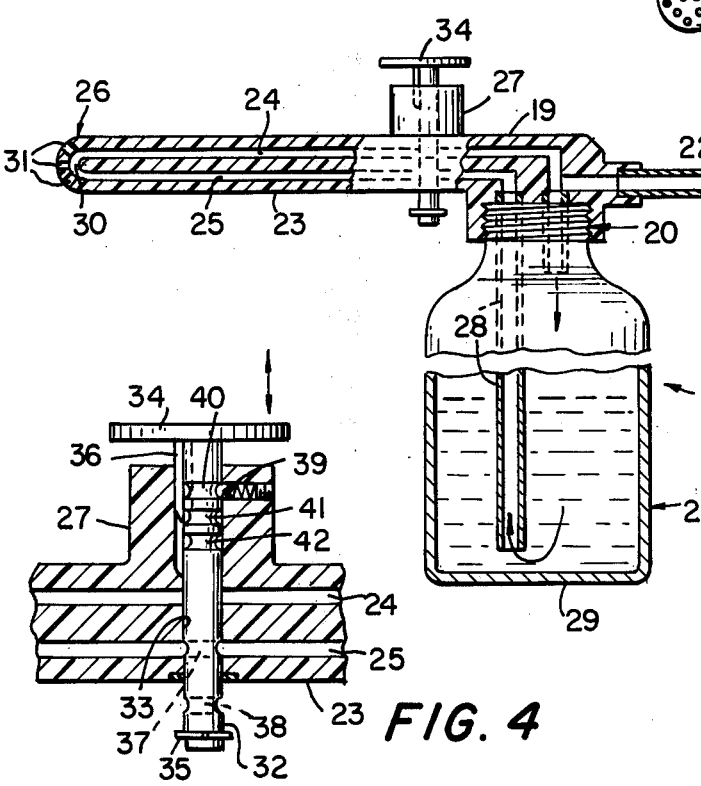

HYGIENE SYSTEM

The present invention relates to a system for oral hygiene and for vaginal hygiene and contraceptive use.

For years, it was felt that mouth washes might be deleterious in that they interfered with normal mouth fluids. However, it has been found that regular daily use of proper mouth washes help maintain a better state of oral hygiene and that specific washes can be formulated to deal with specific problems such as astringent washes for periodontoclasia (pyorrhea) and sodium fluoride or other anti-caries material for the prevention of dental decay.

Similar views were held with respect to douching and spraying of the vaginal tract. Again, today, it is widely felt that better hygine can be established by proper cleansing of this tract. Further, spraying of the vaginal tract with appropriate formulations of liquid may be used for therapeutic purposes and as a contraceptive measure. For example appropriate spraying might be used to eliminate the organism responsible for gonorrhea in women who carry this organism but do not exhibit signs of the disease. In the future, vaginal sprays are expected to find increasing use in contraception either to apply an anti-pregnancy vaccine to the vaginal tract, where absorption can take place, or for the application of chemical contraceptive which may bond to the progesterone receptors in the uterus to prevent implantation of a fertilized ovum or short or long acting anti-spermicides or other contraceptive material.

Examples of prior art devices for oral and vaginal cleansing may be found in U.S. Pat. Nos. 3,870,039; 3,874,506; 3,952,736; 2,482,361; 2,507,214; 2,669,233; 2,903,273; 3,037,505; 3,508,546; 3,762,411; 3,921,635; 4,000,742; and 3,810,465.

None of these U.S. patents discloses the system of the present invention by virtue of which separate oral and vaginal spray devices may be alternatively used in conjunction with a single source of compressed air with the vaginal spray device providing the alternative of a liquid only spray or a mixture of liquid and compressed air.

It is an object of the present invention to provide a system for oral and vaginal hygiene and contraceptive use in which a source of compressed air is utilized to alternatively actuate oral and vaginal spray devices and which is readily adaptable for use in multiple dwelling structures, as well as single dwelling, in which a single source of compressed air is provided for use in connection with devices in a plurality of the dwellings.

The same arrangement is suitable for individual dwellings with a package containing the source of compressed air (e.g. an air compressor), which can be placed in a closet or cupboard, to which tubing for the oral and vaginal spray and irrigation devices can be connected.

According to the invention there is provided a system for oral and vaginal hygiene and for contraceptive use comprising a source of compressed air having a compressed air outlet, an output connector means attached to control flow from the outlet, a first spray device for oral hygiene adapted for connection to the connector means to receive compressed air from the source and a second spray and irrigation device for vaginal hygiene and contraceptive use adapted for connection to the connector means to receive compressed air from the source, wherein the first spray device, which has a first liquid container with a removable spray head connected thereto and an elongate output probe defining an outlet passage leading to a spray nozzle define at one end of the probe, is actuated by compressed air received by way of the connector means to eject a spray of liquid from the container through the nozzle and wherein the second spray device which has a second liquid container with a second removable spray head connected thereto, a second elongate output probe defining a liquid outlet passage and a compressed air outlet passage leading to a spray nozzle at one end of the probe and a control valve mounted in the second spray head for movement between first and second operative conditions to control flow of compressed air and liquid respectively through the compressed air and liquid passages of the second probe, is actuated by compressed air received by way of the connector to eject a spray from the nozzle of the second probe, the spray, with the control valve in its first operative condition, consisting solely of a stream of liquid from the second container and, with the control valve in its second operative condition, consisting of a mixture of liquid from the second container and compressed air.

The invention will now be described, by way of example, with reference to the accompanying drawings, in which:

FIG. 1 is a diagrammatic representation of a multiple dwelling structure having a single source of compressed air with outlet connectors in the bathroom of each dwelling;

FIG. 2 is a part sectioned diagrammatic representation of an oral spray device;

FIG. 3 is a part sectioned diagrammatic representation of a vaginal spray device;

FIG. 4 is a diagrammatic representation of the control valve of the spray device illustrated in FIG. 3;

FIG. 5 is a diagrammatic representation of an outlet connector means for connection of a source of compressed air to spray devices as illustrated in FIGS. 2 and 3;

FIG. 6 is a diagrammatic sectional representation of a distribution valve according to one embodiment of the connector means; and FIG. 7 is a diagrammatic exterior view of a vaginal probe for use as an alternative to the probe illustrated in FIG. 3.

The multiple dwelling structure illustrated in FIG. 1 includes a basement 1 housing an air compressor with compressed air storage tank 2 which is connected by way of a regulator 3 and an air supply line 4 to output connectors 5 in the bathroom 6 of each of the dwellings of the structure. The output connectors are of the type which include automatic shut-off of the compressed air output when devices to which compressed air is supplied are disconnected therefrom.

The oral spray device 7 illustrated in FIG. 2 includes a spray head 8 which is removably attached by screw threads (not shown) in a sealed manner to a generally cylindrical liquid container 9. The spray head 8 has an inlet tube 10 adapted for connection to the connector 5 and is arranged to supply compressed air received from the connector 5, when on/off valve 11 is open to the interior of the container 9 adjacent the neck 12 of the container 9 which carries the screw threads by which the spray head 8 is attached. The spray head 8 also includes an elongated probe 13 which defines an outlet passage 14 extending to a nozzle 15 at the end of the probe 13. The end of the outlet passage 14 remote from the nozzle 15 communicates by way of a tube 16 with the portion of the container 9 adjacent the end 17 of the container remote from the neck 12.

With the inlet tube 10 connected to the connector 5 the compressed air passes, when on/off valve 11 is open, into the container 9 to pressurize the container 9 thereby to force liquid from the container 9 through the tube 16 and outlet passage 14 to the nozzle 15 where the liquid is ejected as a spray.

The vaginal spray device 18 consists of a spray head 19 which is removably attached in pressure type manner by screw threads 20 to a liquid container 21. The spray head 19 includes an inlet tube 22 adapted for connection to connector 5 to receive compressed air from the compressor 2, an elongate probe 23 which defines a compressed air passage 24 and a liquid outlet passage 25 which extends along the probe 23 from a nozzle arrangement 26 disposed at one end of the probe by way of a control valve 27 to communicate, in the case of the compressed air passage 24, with the interior of the inlet tube 22 and, in, in the case of the liquid outlet passage 25, to the interior of the tube 28 which extends from the spray head 23 into the container 21 to a portion of the container 21 adjacent the end 29 thereof which is remote from the screw threads 20.

The nozzle arrangement 26 consists of a mixing chamber 30 with which the passages 24 and 25 communicate and from which a plurality of spray nozzles 31 extend to the exterior of the probe 23.

The control valve 27 forms part of the spray head 19 and consists of a spool 32 captively mounted in a bore 33 which extends through the probe 23 transversely of and intersecting passages 24 and 25. To one end of the spool is mounted a control knob 34 to facilitate manual movement of the spool while at the other end of the spool is a spring retainer 35 housed in an annular groove formed in the periphery of the spool. The knob 34 and retainer 35 together serve to restrict longitudinal movement of the spool relative to the probe 23. Rotation of the spool about its axis relative to the probe is prevented by a key and keyway 36 the tolerances of which permit longitudinal movement of the spool along its axis relative to the probe 23. The key is attached to the spool while the keyway is formed in the probe.

The valve is provided with three operative positions, in the first of which (as illustrated in FIG. 4) the air passage 24 is closed by the spool while the liquid passage 25 is open for flow of liquid therethrough by way of a transverse passage 37 in the spool and in the second of which transverse passage 37 is aligned with air passage 24 and a transverse passage 38 is aligned with the liquid passage 25 thereby to allow flow through both passages 24 and 25. The third operative position of the control valve is a position intermediate the first and second positions in which both passages 24 and 25 are closed by the spool 32. The spool is located in the three operative positions by means of a spring loaded ball detent 39 coming into engagement with annular grooves 40, 41 and 42. With the valve in its first operative position the detent 39 is in engagement with annular groove 40, in the second operative position detent 39 is engaged with annular groove 42 while in the third and intermediate position the detent 39 is engaged with the groove 41.

In the vaginal spray device illustrated in FIGS. 3 and 4 compressed air received from a connector 5 passes by way of the inlet tube 22 to passage 24 and to the interior of the liquid container 21 adjacent the screw threads 20. The compressed air entering the container 21 drives liquid therein through the tube 28 into the tube 25. In the use of this device the user has the option of placing the control valve in its first operative position in order to produce a stream from the nozzle arrangement 26 which consists solely of the liquid ejected from the container 21 or of producing, or when the control valve is in its second operative position, a spray from the nozzle arrangement 26 which consists of liquid driven from the container 21 mixed with compressed air passing by way of the valve 27 along the passage 24.

FIG. 5 is a diagrammatic representation of an arrangement in which the connector 5 includes a control valve 43 controlling supply of compressed air from the air line 4 to two outlets 44 and 45 to which are connected an oral spray device in accordance with FIG. 2 and a vaginal spray device according to FIGS. 3 and 4. The control valve 43 consists of a body having the outlets 44 and 45 in a bore of which is housed a valve member 46 movable to positions in which the outlet 44 alone, the outlet 45 alone or neither of outlets 44 and 45 are connected to the air line 4.

As shown in FIG. 7 the form of probe utilized in FIG. 3 may be replaced by a probe having a large plurality of spray nozzles 31 all connected to the mixing chamber 30.

It will be appreciated that while the present invention has been particularly described with reference to a multiple dwelling system having a central air compressor supply, the invention is equally applicable to an arrangement in which a portable or permanent air compressor with or without compressed air storage facilities is associated with alternatively usable spray devices such as those described with reference to FIGS. 2 and FIGS. 3 and 4.

I claim:

1. A system for oral and vaginal hygiene and for contraceptive use comprising a source of compressed air having a compressed air outlet, an output connector means attached to control flow from the outlet, a first spray device for oral hygiene adapted for connection to the connector means to receive compressed air from the source and a second spray device for vaginal hygiene and contraceptive use adapted for connection to the connector means to receive compressed air from the source, wherein the first spray device, which has a first liquid container with a removable spray head connected thereto and an elongate output probe defining an outlet passage leading to a spray nozzle defined at one end of the probe, is actuated by compressed air received by way of the connector means to eject a spray of liquid from the container through the nozzle and wherein the second spray device, which has a second liquid container with a second removable spray head connected thereto a second elongate output probe defining a liquid outlet passage and a compressed air outlet passage leading to a spray nozzle at one end of the probe and a control valve mounted in the second spray head for movement between first and second operative conditions to control flow of compressed air and liquid respectively through the compressed air and liquid passages of the second probe, is actuated by compressed air received by way of the connector to eject a spray from the nozzle of the second probe, the spray, with the control valve in its first operative condition, consisting solely of a stream of liquid from the second container and, with the control valve in its second operative condition, consisting of a mixture of liquid from the second container and compressed air.

2. A system according to claim 1 wherein the source of compressed air is a compressor with air storage tank, the connector means is of the quick detach type which is automatically closed when no device is connected thereto and the first and second spray devices are arranged for connection alternatively to the connector means.

3. A system according to claim 1 wherein the source of compressed air is an air compressor with attached compressed air storage chamber, the output connector means has two outlets and a valve having three operative conditions in a first of which one of the connector means outlets is connected to the compressed air outlet, in a second of which the other of the connector means outlets is connected to the compressed air outlet and in the third of which neither of the connector means outlets is connected to the compressed air outlet, and the first and second spray devices are connected respectively to the one and the other of the connector means outlets.

4. A system according to claim 1 wherein control valve of the second spray device has a third operative position, intermediate the first and second operative positions in which both compressed air and liquid from the second liquid container are prevented from reaching the nozzle means of the second elongate output probe.

5. A system according to claim 4 wherein the second elongate output probe defines a compressed air passage extending from the nozzle by way of the control valve to the interior of the second liquid container and to an inlet to receive compressed air from the source and a liquid carrying passage extending from the nozzle by way of the control valve to a position in the second liquid container below the liquid level of that container.

6. A system according to claim 5 wherein the control valve is a spool valve the spool of which extends, and is movable between its three operative positions, transversely of and intersecting the compressed air and liquid passages, the spool having longitudinally spaced transverse passages positioned to allow flow through the compressed air and liquid passages in dependence upon the operative position of the valve, the control valve also having spring loaded detent and groove means to resiliently locate the valve spool in each of its three operative positions.

7. A system according to claim 1 wherein the first spray device as an on/off valve to control flow of compressed air to the device.

* * * * *